United States Patent [19]

Holtkamp, Sr.

[11] Patent Number: Plant 6,109

[45] Date of Patent: Feb. 16, 1988

[54] AFRICAN VIOLET PLANT NAMED IMPROVED ATLANTA

[75] Inventor: Reinhold Holtkamp, Sr., Isselburg, Fed. Rep. of Germany

[73] Assignee: Gesellschaftsvertrag uber die Erfindergemeinschaft "Optimara", Rees Haffen, Fed. Rep. of Germany

[21] Appl. No.: 823,516

[22] Filed: Jan. 28, 1986

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named Improved Atlanta having strong upright flower stems, two of which appear at each leaf axil; light pink flowers; dark green leaves with light green centers; vigorous growth habit; early and profuse flowering; long-lasting, non-dropping flowers which form a tight flower head above the foliage.

1 Drawing Figure

The present invention comprises a new and distinct cultivar of African violet plant, botanically known as *Saintpaulia ionantha*, and hereinafter referred to by the cultivar name Improved Atlanta.

The new cultivar was originated from a cross made in a controlled breeding program in Isselburg, West Germany. The female, or seed parent was a cultivar designated 349 light pink girl. The male, or pollen parent was a cultivar designated 68 red single.

Improved Atlanta was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and retained through successive generations of asexual reproduction.

Improved Atlanta has not been observed under all possible environmentl conditions. The phenotype may vary significantly with variations in environment such as temperature, light intensity and day length. The following observations, measurements and values describe the new cultivar as grown in Isselburg, West Germany and Nashville, Tenn. under greenhouse conditions which closely approximate those generally used in commercial practice.

The following traits have been repeatedly observed and are determined to be basic characteristics of Improved Atlanta, which in combination distinguish this African violet as a new and distinct cultivar:

1. Strong, upright flower stems curving toward the center.
2. A unique feature of Improved Atlanta is that out of each leaf axil two flower stems appear, one before the other. This results in a continuous blooming multiflora.
3. The flower head builds in three visible incremental steps that flower 14 days apart.
4. Profuse flowering.
5. Each plant carries up to 7 and more upright flower stems, each of which carries 8–12 flowers.
6. Vigorous grower.
7. Plant is saleable 8 to 9 weeks after potting.
8. Dark green velvet leaves, slightly hairy.
9. Long-lasting, non-dropping single light pink flowers.

10. Seed capsule pushes slightly through.
11. Very attractive girl-type leaves that are strongly serrated with a bright green center.
12. After maturity, the flowers dry off and remain on the peduncle without becoming infected by botrytis.
13. When compared with the cultivar Atlanta, disclosed in U.S. Plant Pat. No. 4,875, the new cultivar is principally distinguished by its novel flower stem production. The flower color and leaf form and color are similar for both varieties.

The accompanying photographic drawing shows a typical specimen plant of the new cultivar grown in a 10 cm. pot. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions in Nashivlle, Tenn. Under cooler temperatures or more intensive lighting, the pink flower color will tend to intensify.

Botanical classification: *Saintpaulia ionantha*, Ramat., cv. Improved Atlanta.

Parentage:

*Male parent.*—68 red single.

*Female parent.*—349 light pink girl.

PROPAGATION

The new cultivar holds its distinguishing characteristics through successive propagations by leaf cuttings.

PLANT

From 8 cm. to 10 cm. tall when grown in pots, and approximately 24–26 cm. in diameter when fully grown.

Leaves:

*Shape.*—Generally round, with light green (girl type) centers; heave indentations and serrated.

*Diameter.*—65–75 mm. wide.

*Texture.*—Velvety, very shiny.

*Ribs and veins.*—Under side, wall pronounced, very shiny, light green. Color between veins has a touch of purple.

*Color (upper side).*—147A.

*Color (under side).*—148D.

*Petioles.*—Strong, upright, hairy, brownish purple.

Flowers:

*Buds.*—Size: 8–10 mm. just before opening. Shape: Ball-shaped. Color: Dark brown.

*Sepals.*—Shape: Spear-shaped, hairy; five in number.

*Calyx.*—Basifixed.

*Peduncle.*—Character: Strong, upright, hairy. Color: Brownish.

Individual flowers:

*Size.*—40–45 mm. in diameter.

*Shape.*—Single, violet-shaped; occasionally an additional single leaf petiole appears in center.

*Color* (*upper side*).—69B-C; several flowers in photo appear almost white, although indicated color values are correct.

*Color* (under side).—69C.

*Borne.*—Each flower stem carries 8–12 flowers on a strong, upright peduncles that curve toward center of plant.

Flowering habit: Flowers early and profusely, with the compact flower head carried well above the leaves.

Reproductive organs:

*Stamens.*—Two.

*Anthers.*—Two, with four anther cells.

*Filaments.*—Light pink.

*Styles.*—6 mm., dark purple, with a light green base.

Roots: Normally developed, white when young, turning slightly brownish when older.

Disease resistance: Good.

I claim:

1. A new and distinct cultivar of African violet named Improved Atlanta, as illustrated and described, and particularly characterized by its strong upright flower stems, two of which appear at each leaf axil, light pink flowers, dark green leaves with light green centers, vigorous growth habit, early and profuse flowering, and by its long-lasting, non-dropping flowers which form a tight flower head above the foliage.

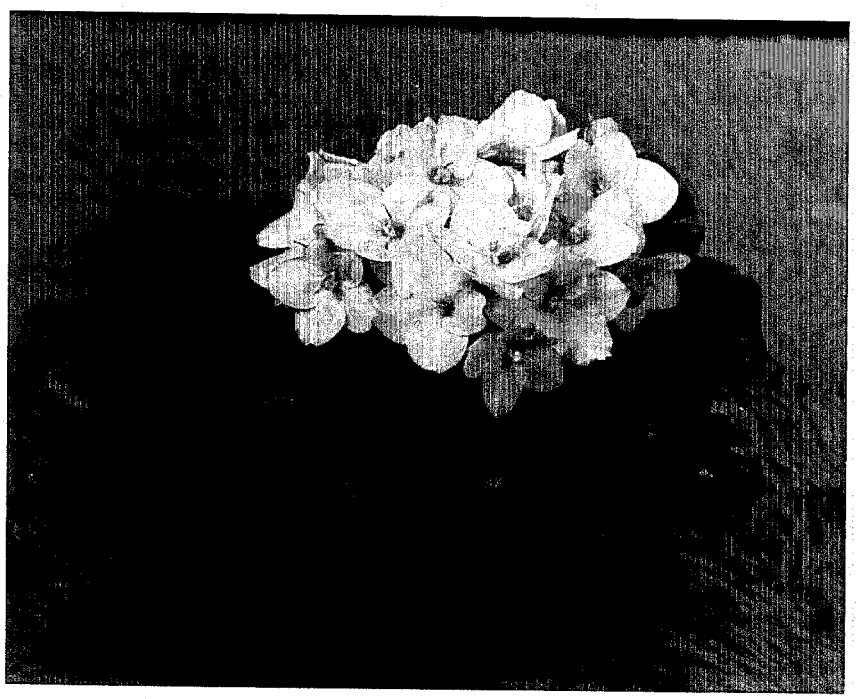

* * * * *